United States Patent
Sønderholm et al.

(10) Patent No.: US 8,615,824 B2
(45) Date of Patent: Dec. 31, 2013

(54) STOOL COLLECTOR

(75) Inventors: Morten Høstrup Sønderholm, Aarhus (DK); Henning Hedegaard, Sunds (DK); Christian Emil Erfurt-Hansen, Aarhus (DK); Søren Peter Søgaard, Haderslev (DK); Lars Erik Lund, Vejle (DK)

(73) Assignee: GP Medical Devices ApS, Sunds (DK)

( * ) Notice: Subject to any disclaimer, the term of this patent is extended or adjusted under 35 U.S.C. 154(b) by 0 days.

(21) Appl. No.: 12/736,632

(22) PCT Filed: Apr. 14, 2009

(86) PCT No.: PCT/DK2009/050092
§ 371 (c)(1),
(2), (4) Date: Jun. 8, 2011

(87) PCT Pub. No.: WO2009/129813
PCT Pub. Date: Oct. 29, 2009

(65) Prior Publication Data
US 2011/0270125 A1    Nov. 3, 2011

(30) Foreign Application Priority Data

Apr. 25, 2008  (DK) ............................... 2008/050095
Oct. 10, 2008  (DK) ............................... 2008/000356

(51) Int. Cl.
*A47K 11/06*    (2006.01)

(52) U.S. Cl.
USPC .................................... 4/484; 4/661; 4/144.2

(58) Field of Classification Search
USPC .......... 600/562; 604/317–322, 334, 349, 403; 4/144.1–144.2, 243.2, 661
See application file for complete search history.

(56) References Cited

U.S. PATENT DOCUMENTS

| | | | | |
|---|---|---|---|---|
| 4,445,235 A | * | 5/1984 | Slover et al. | 4/144.2 |
| 4,760,613 A | * | 8/1988 | Bobak | 4/243.2 |
| 4,975,990 A | * | 12/1990 | Chan | 4/245.1 |
| 5,060,317 A | * | 10/1991 | Bertelsen | 4/144.2 |
| 5,412,819 A | * | 5/1995 | Matusewicz et al. | 4/661 |
| 5,463,782 A | * | 11/1995 | Carlson et al. | 4/661 |
| 7,996,926 B2 | * | 8/2011 | Aguila | 4/144.1 |

FOREIGN PATENT DOCUMENTS

| | | | | |
|---|---|---|---|---|
| DE | 29613596 | | 9/1996 | |
| DE | 29807188 | | 9/1998 | |
| DE | 10052879 | | 5/2002 | |
| DE | 102006045373 | | 3/2007 | |
| FR | 2740672 | | 5/1997 | |
| WO | WO 2007065429 | * | 6/2007 | ............. A61F 5/445 |

* cited by examiner

*Primary Examiner* — Max Hindenburg
*Assistant Examiner* — Renee Danega
(74) *Attorney, Agent, or Firm* — James Creighton Wray

(57) ABSTRACT

A stool collector adapted for being positioned in a use position in which it is secured to a standard water closet or toilet to collect a stool sample delivered by a user, said stool collector comprising a rear piece adapted for being secured between rear halves of a toilet bowl and a tip-up toilet seat, respectively, of said toilet. The stool collector further comprises a front piece adapted for being secured between front halves of said toilet bowl and said tip-up toilet seat, respectively, said front piece comprising two lateral wings enclosing a cut-out adapted to allow for urine from said user to pass through into said toilet bowl in said use position, and an intermediate piece connecting said front and rear pieces and in said use position forming a stool collecting area adapted to receive said stool sample, said front, rear and intermediate pieces being manufactured from a flexible, foldable, biodegradable and highly water soluble paper material, said stool collector thus being suitable for being flushed in a standard water closet.

17 Claims, 4 Drawing Sheets

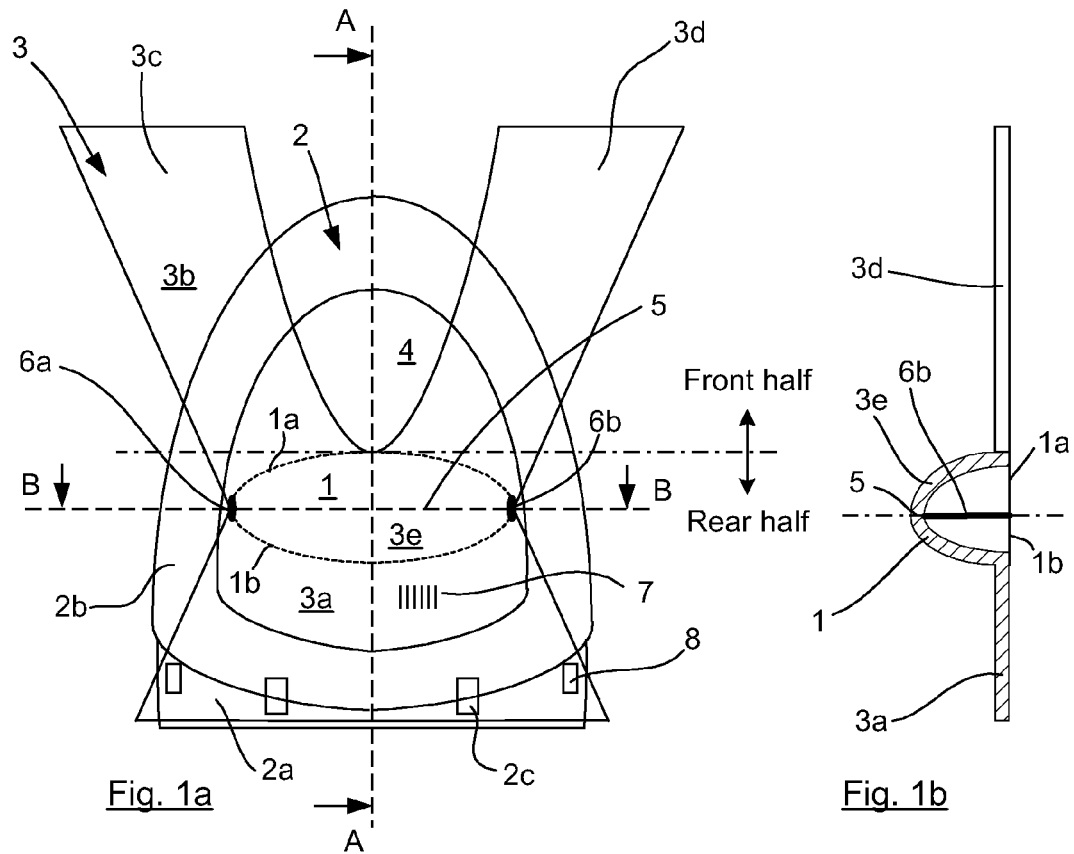
Fig. 1a
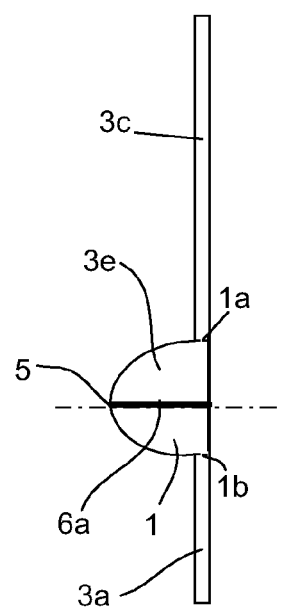
Fig. 1b
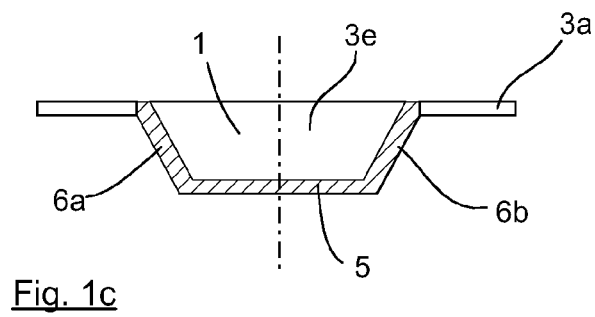
Fig. 1c
Fig. 2

STOOL COLLECTOR

This application claims the benefit of Danish Application No. 2008/050095 filed Apr. 25, 2008, Danish Application No. 2008/000356 filed Oct. 10, 2008, and PCT/DK2009/050092 filed Apr. 14, 2009, which are hereby incorporated by reference in their entirety as if fully set forth herein.

The present invention relates in a first aspect to a stool collector according to the introductory part of claim 1. In a second aspect, the invention relates to a method for obtaining a stool specimen according to claim 13.

Within the health sector, stool specimens are widely used for screening and diagnosing. To obtain stool specimens, no intervention in the human body is required and the presence of a range of substances or organisms may be indicative of various diseases or disorders.

The obvious advantages notwithstanding, significant inconveniences are encountered, however, when it comes to the collection of stool specimens. Depending on its texture, a stool specimen may be difficult to gather into a stool container suitable for being transported to a laboratory for carrying out treatment and/or analysis of the contained stool.

Sanitary problems must also be taken into account. Especially when dealing with specimens acquired due to a suspicion of contagious disease, the very obtaining of the specimen may involve a significantly augmented risk of disease transmission, notably in a case, where the patient is solely responsible for the specimen-obtaining procedure. Furthermore, the uninviting aesthetic qualities of stool, notably its odour, add to the problems associated with the gathering of samples.

Conventionally, somewhat unhygienic methods are used to obtain stool specimens. Typically, sheets of cellophane or strips of paper stretched across a water closet (cf. e.g. WO 2004/075757), if not bedpans or cups placed within the toilet bowl, are targeted at defaecation, whereupon it is left to paramedical staff or the patient to transfer a required amount of stool into a container suitable for the ensuing analysis. Said transferal takes place by pouring or scraping stool from the targeted item into the chosen container, possibly via an intermediate container and often followed by cleaning and sterilization of the hands and applied utensils.

U.S. Pat. No. 6,415,455 discloses an apparatus for collecting, storing and/or shipping a stool specimen, which apparatus comprises a housing with a retractable bag for collecting a specimen.

U.S. Pat. No. 4,309,782, on which the introductory part of claim 1 is based, discloses a device for collecting a faecal specimen, which device is made from a biodegradable material. The device is provided with a collection bag, wherein the specimen is deposited. The collection bag is enclosed by a foldable base plate, which in use covers a rear part of a toilet bowl rim to permit discharge of urine at the front part. The collection bag is open at its rear part such that superfluous stool can be scraped through the opening into the toilet after which the device is being traditionally disposed of by throwing it into a garbage can or the like.

The above devices of the prior art, however, do not alleviate the need for cumbersome cleaning and/or cumbersome disposal procedures when obtaining the stool specimen. Thus, problems of hygiene and discomfort associated with the handling of stool and stool infected collecting tools persist.

In view of the above, the object of the present invention is to provide a stool collector and a method for obtaining a stool specimen, which collector and method are readily applicable and minimize the risk of infection and spreading of diseases, and which collector is furthermore easier to dispose of. Further, said collector and method should be safe, affordable, cost-efficient, environmentally acceptable, simple and robust.

To meet this object, according to the first aspect of the invention the stool collector is characterized by the features of the characterizing part of claim 1.

The front piece with two lateral wings strengthens the attachment of the stool collector to the toilet in the use position because the area of the stool collector, which can be positioned between the toilet seat and the rim of the toilet bowl, is larger. The positioning of an intermediate, stool-collecting piece connecting the front and rear parts allows for additional support of the intermediate piece while still allowing for urine to pass through during use. Thus, it is ensured that a front part of the water closet opening is left uncovered by the stool collector for free passage of urine into the water closet, the collector (or in practice rather the intermediate piece of the collector) hence only covering a rear part of the water closet opening. In this way it is avoided that urine be intercepted by the stool collecting area and thus mixed with the stool specimen, which would otherwise render the latter useless for the purpose of analysis. Also, the strength of the wet paper material would be destroyed.

In the present context the term "highly water soluble" is used for paper types, which in moving water, i.e. when flushed in a toilet, defibrate in less than about 20 minutes. Paper materials of today having this property do not have the required strength to be applied as the manufacturing material of prior art stool collector structures. With the prior art structures a stool collector manufactured from a highly water soluble paper material to make it suitable for being flushed in a toilet would face a significant risk of collapsing under the weight of the stool deposited on them.

However, the strengthening of the structure of the stool collector by means of lateral wings makes it possible to manufacture the stool collector from less strong materials because the stool collecting area is positioned between two attached pieces, i.e. the front and the rear pieces.

With the present invention it is thus possible to manufacture the stool collector from a highly water soluble paper material, providing for a stool collector that may readily be disposed of in a hygienic manner by flushing in a standard toilet upon use. Also, the stool collector has sufficient strength to be retained securely on the water toilet bowl during use.

In this way an inexpensive, simple stool collector is provided that is particularly easy to dispose of and with which collector hygiene is improved and workload reduced. The collector is easy to use for patients as well as paramedical staff and the possibility of greatly reducing cleaning and sterilization is opened up. Furthermore, manufacture of the collector requires only a modest consumption of energy and raw materials.

The dependent claims provide preferred embodiments of the invention.

In a preferred embodiment of the first aspect of the invention said front, rear and intermediate pieces are manufactured from the same material, preferably they have been cut from one plane piece of said paper material. This provides for low-cost manufacturing as well as easy and compact folding, packing and unpacking of the stool collector. The preferred way of making cutting from one piece of paper material possible is forming said intermediate piece by a transverse centre folding, an attachment, preferably a linear gluing line, connecting opposite peripheral portions of said intermediate piece to form said stool collecting area, said stool collecting area forming a downwards depression in said use position. In a further development of this embodiment said intermediate piece has a transverse dimension equal to or smaller than an associated transverse dimension of said toilet bowl in said use position, such that said intermediate portion in said use position is adapted to hang from said front and rear pieces. In another development of the present embodiment the stool collector further has an axial centre line, preferably a line of symmetry, extending from a rear edge to a front edge of said stool collector, and wherein, when measured on said stool collector in a non-folded position, i.e. in which said peripheral attachments are released:

said intermediate piece has a length, i.e. a dimension parallel to said centre line between front and rear edges of said peripheral attachment, of 140-360 mm, preferably 170-230 mm, and a largest width measured perpendicularly to said centre line of 320 mm, preferably 280 mm, said rear piece has a length, i.e. a dimension parallel to said centre line between said rear edge of said peripheral attachment and a rear edge of said stool collector, of 190-270 mm, preferably 210-250 mm, said wings have a length, i.e. a dimension parallel to said centre line between said front edge of said peripheral attachment and a front edge of said stool collector, of 200-320 mm, preferably 240-280 mm, and said cut-out has a length, i.e. a dimension parallel to said centre line, of 190-270 mm, preferably 210-250 mm.

These dimensions makes the stool collector ideal for use with a common, ordinary, standard toilet or water closet.

In another embodiment said front and rear pieces comprise edges suitable for being folded down at an exterior of said toilet bowl. Optionally, the means for attachment are provided with marks to indicate one or more suitable lines of folding.

In another embodiment said front and rear pieces are adapted for contact with at least 60%, preferably at least 75%, more preferably at least 90%, of a total circumference of an upper rim of said toilet bowl in order to further strengthen the attachment to the toilet bowl.

In another embodiment said paper material is adapted to defibrate in less than 20 minutes, preferably between 8 and 12 minutes when being flushed in said toilet. Such a paper material may e.g. be a semi wet-strong paper material. By using a paper material, which is defibratable and soluble in water in motion (and not when still), it is ensured that the stool collector will dissolve quickly when flushing it in the toilet to ensure that the sewer system is not clogged. Simultaneously, the paper material will not dissolve—at least for a sufficient period of time—when exposed to still liquids such as those resulting from an amount of stool being deposited on the stool collector. Thus, the stool collector may be disposed of by flushing it in a water closet without risk of clogging the drain.

The paper material of the stool collector preferably has at least one, and more preferably all, of the following properties:

a weight of at least 23 g/m$^2$, preferably between 23 g/m$^2$ and 50 g/m$^2$, a longitudinal pull strength of at least 1.5, preferably between 1.5 and 4.6, according to the SCAN P-67 standard, a longitudinal tear strength of at least 125, preferably between 125 and 350, according to the ISO 1974 standard, a transversal pull strength of at least 0.7, preferably between 0.7 and 2.0, according to the SCAN P-67 standard, and a transversal tear strength of at least 210, preferably between 210 and 450, according to the ISO 1974 standard.

In another embodiment at least one of said rear piece, front piece and intermediate piece comprises a plurality of perforations suitable for allowing air trapped inside the stool collector to escape when flushed in a water closet, each perforation preferably having a diameter of more than 0.1-1 mm and a linear length of 2-50 mm. The number of perforations may vary such that the smaller the diameter of each perforation the greater the total number of perforations. For example there may be provided 1 to 15 perforations per cm$^2$. The perforations can be cut through only part of the paper material, e.g. about half-way through, to maintain sufficient strength.

In a specific embodiment, the stool collecting area is provided with an anti-friction coating, preferably consisting of a biodegradable material. In this way, the flow of stool towards and into the stool collecting area is enhanced.

According to a further embodiment said rear piece comprises a substantially straight rearwards edge, an adhesive adapted for attaching said stool collector to said toilet bowl being provided on said rear piece near said rearwards edge, said tip-up toilet seat adhesive preferably being arranged at the corners of said rearwards edge. The inventors have found that the risk of wet urine residues deposited on the upper rim of the toilet bowl is smaller at the corners than at the centre part of rearwards edge of the toilet bowl rim.

To meet the aforementioned object, according to a second aspect of the invention a method for obtaining a stool specimen is provided, said method comprising the steps of providing a stool collector according to any one of the previous claims;

attaching said stool collector between a toilet bowl and a tip-up toilet seat or on top of a tip-up toilet seat of a water closet or toilet; and positioning and flushing said stool collector in said water closet.

The method according to the second aspect of the invention provides the same or similar advantages as the first aspect of the invention.

In a specific embodiment of the second aspect of the invention, the method further comprises the steps of depositing a stool specimen by defaecation on the stool collecting area and transferring a stool specimen to a stool container, preferably a stool tube.

In the following, preferred embodiments of the invention will be illustrated by reference to the schematic and non-limiting figures, which show embodiments of the stool collector according to the first aspect of the invention. The illustrated stool collectors are suitable for being applied to carry out the method according to the second aspect of the invention.

BRIEF DESCRIPTION OF THE DRAWINGS

FIG. 1a shows a plane view seen from above of a first embodiment of a stool collector according to the first aspect of the present invention attached to a standard water toilet, FIGS. 1b and 1c show sectional views along the lines A-A and B-B, respectively, of the stool collector of FIG. 1a, FIG. 2 shows a side view of the stool collector of FIG. 1a, FIG. 3 shows a plane view of the stool collector of FIG. 1a, in which gluing lines have been released.

DETAILED DESCRIPTION OF THE PREFERRED EMBODIMENTS

Figure 3:
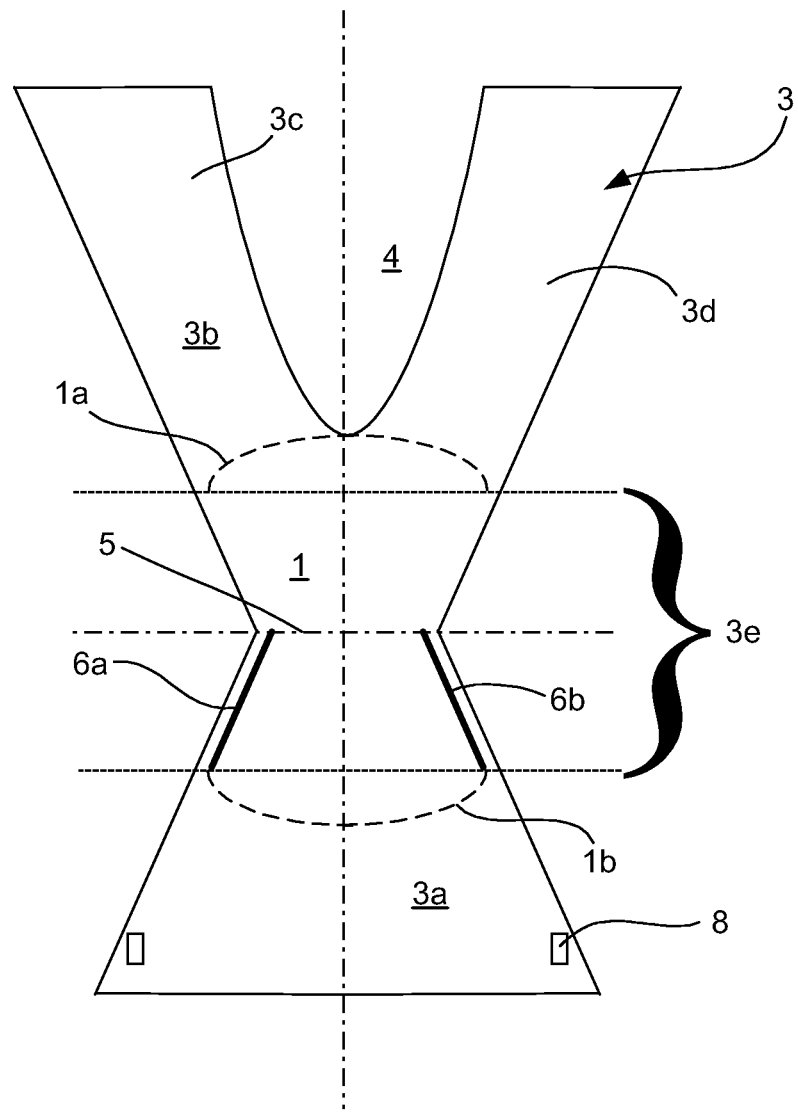

FIGS. 1a to 1c and 2 show different views of a stool collector 3 according to the first aspect of the present invention in a use position in which it is secured to a standard water closet or toilet 2 (only shown in FIG. 1a) to collect a stool sample to be delivered by a user. The stool collector 3 is designed so as to fit a standard water closet or water toilet for adults. However, the stool collector according to the invention may be adapted to fit standard toilets designed for children and/or for adults. A standard or common water closet or toilet comprises a toilet bowl with an upper rim, which is typically substantially ellipsoidal or oval. A tip-up toilet seat of substantially corresponding shape is attached thereto so as to be able to cover the upper rim of the toilet bowl for a user to sit on. The tip-up toilet seat can be tipped up to an upward position, revealing the upper rim of the toilet bowl. On top of the toilet seat a tip-up toilet cover may be positioned. A water cistern for flushing the toilet bowl is positioned in vicinity of the toilet bowl, typically in a position above and abutting the toilet bowl at a rearward end of the toilet bowl, the tip-up toilet seat, and optionally the cover, resting against the cistern in the tipped up position.

In FIG. 1a the stool collector 3 is shown positioned between a tip-up toilet seat 2b and an upper circumferential rim of a toilet bowl 2a of the toilet 2. The toilet seat 2b is hinged to a rear part of an upper rim of the toilet bowl 2a by means of hinges 2c. The upper circumferential rim of the toilet bowl 2a has an oval shape to which the shape of the toilet seat 2b corresponds. More specifically, the circumferential upper rim of the toilet bowl 2a comprises two lateral curved rim segments, a curved front segment connecting one pair of ends of the lateral rim segments and a straight rear portion connecting the other pair of ends of the lateral rim segments. The shape of the toilet seat corresponds thereto, except from a rear portion, which in this case is curved.

The stool collector 3 comprises a rear piece 3a, which in FIG. 1a is secured between rear halves of the toilet bowl 2a and toilet seat 2b, respectively. The rears halves and front halves of the toilet bowl 2a and toilet seat 2b, respectively, are separated in FIG. 1a by means of a dash-dot line. A rearwards edge of the rear piece 3a is substantially straight, such a configuration corresponding to the straight rear segment of the toilet bowl 2a.

The stool collector 3 further comprises a front piece 3b adapted for being secured between the front halves of the toilet bowl 2a and toilet seat 2b, respectively. The front piece 3b comprises two lateral wings 3c, 3d enclosing a cut-out 4 adapted to allow for urine from the user to pass through into the toilet bowl 2a. The exact shape and size of the cut-out 4 is not crucial as long as it serves the purpose of providing an uncovered region 4 of sufficient size to allow for unrestricted passage of urine into the toilet bowl 2a.

Finally, as is seen best in FIG. 3, the stool collector 3 comprises an intermediate piece 3e, which connects the front piece 3b and rear piece 3a. The intermediate piece 3e forms a stool collecting area 1 adapted to receive a stool sample from the user. The intermediate piece 3e is situated between the front piece 3b and the rear piece 3a, the front piece 3b and rear piece 3a also contributing to form the stool collecting area 1 as is shown by the lines 1a and 1b in FIG. 3. The stool collecting area 1 is shaped as a depression that in FIG. 1 is shown having an oval cross-sectional shape when seen from above as defined by the lines 1a and 1b. Also the intermediate piece 3e may consist solely of the stool collecting area 1.

In the use position shown in FIGS. 1a-1c and 2 the front piece 3b and rear piece 3a have been pulled apart while lying in the plane of the upper rim of the toilet bowl 2a, such that the stool collecting area 1 is expanded as a pocket-like depression extending downward from said plane into the toilet bowl 2a. Thus, the folding line 5 defines a lower periphery of the downward extending pocket that is the stool collecting area 1. An attachment in the form of two linear gluing lines 6a, 6b connect opposite peripheral portions of the intermediate piece 3e to form the stool collecting area 1. Thus, the gluing lines 6a, 6b as well as curved parts of the intermediate piece 3e, the front piece 3b and the rear piece 3a define the sides of the stool collecting area 1.

Figure 4A:
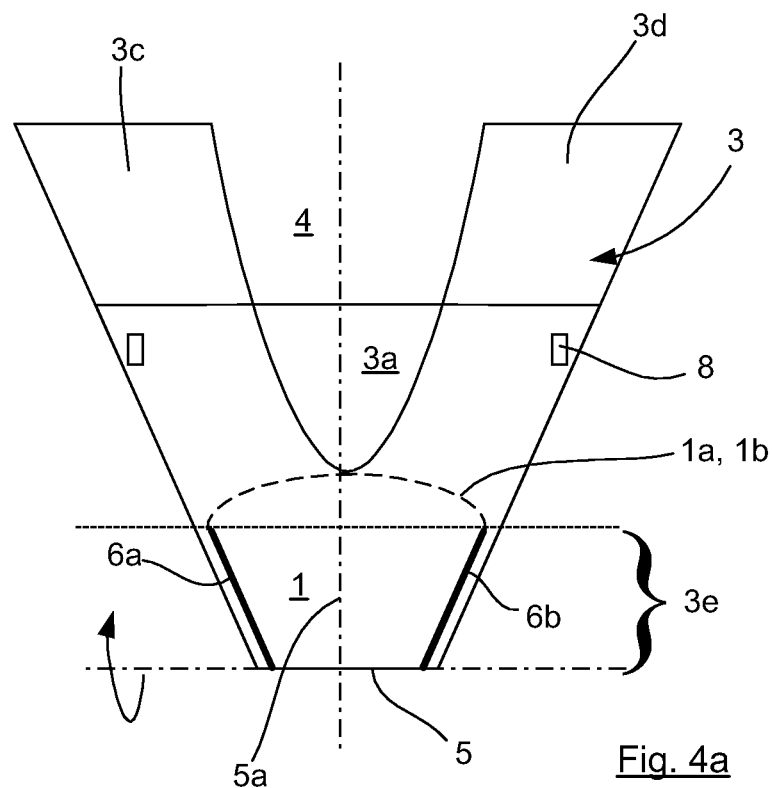
FIGS. 4a to 4c show plane views of the stool collector of FIG. 1a, in which the gluing lines are active, and the stool collector has been folded one, two, and three times, respectively, with a view to packing of the stool collector.

In FIG. 3 the gluing lines 6a, 6b are released, and all parts of the stool collector lie flat in the same plane. During manufacture of the stool collector 3 the gluing lines 6a, 6b are applied to peripheral areas of the intermediate piece 3e, after which opposite parts of the intermediate piece are brought together. FIG. 4a shows the rear part of the stool collector 3 folded from the plane, non-folded position of FIG. 3 along a transverse centre folding line 5 to lie in a plane with the upper part of the stool collector, whereby the gluings 6a, 6b are completed. The attachment need not be gluing lines, but can take other forms such as point gluings, crease connections or foldings; important is only that the sides of the intermediate piece 3e are connected.

As is seen best in FIG. 3, the intermediate piece 3e tapers linearly from its largest width at the transitions to the front piece 3b and the rear piece 3a, respectively, towards a smallest width at the transverse centre folding line 5. In the use position shown in FIG. 1a the smallest width is smaller than an associated transverse dimension of the toilet bowl 2a, such that the intermediate portion 3e in the use position hangs from the front and rear pieces 3b, 3a.

The stool collector has an axial centre line of symmetry (coincident with the section A-A in FIG. 1a), extending from a rear edge to a front edge of the stool collector 3. When measured on the stool collector 3 in the non-folded, plane position of FIG. 3 (in which the gluings 6a, 6b are released):

the intermediate piece 3e has a length, i.e. a dimension parallel to said centre line between front and rear edges of the gluings 6a, 6b, of about 200 mm, and a largest width measured perpendicularly to said centre line of 270 mm, the rear piece 3a has a length, i.e. a dimension parallel to said centre line between said rear edge of the gluings 6a, 6b and a rear edge of the stool collector 3, of about 230 mm, the wings 3c, 3d have a length, i.e. a dimension parallel to said centre line between said front edge of the gluings 6a, 6b and a front edge of the stool collector 3, of about 260 mm, and the cut-out 4 has a length, i.e. a dimension parallel to said centre line, of about 220 mm.

For illustrative purposes in FIGS. 1b, 1c and 2 the thickness of certain parts of the front piece 3b, rear piece 3a, intermediate piece 3e and gluings 6a, 6b has been greatly exaggerated.

In use, the stool collector 3 covers about 70-80% of the total circumferential area of the toilet bowl 2a upper rim. This provides for a large attachment area between the toilet seat 2b and the toilet bowl 2a and thus a stronger attachment all in all.

The front and rear pieces 3b, 3a are dimensioned such that outer sections thereof extending beyond the upper rim of the toilet bowl 2a may be folded down at the exterior of the toilet bowl 2a (not shown in the figures) such as by use of the parts of pieces 3b, 3a lying outside the outer periphery of the upper rim of the toilet bowl 2a in FIG. 1a.

The region 4 left uncovered by the stool collector 3 constitutes about 20-50% of the area of the total toilet bowl opening.

Figure 4B:
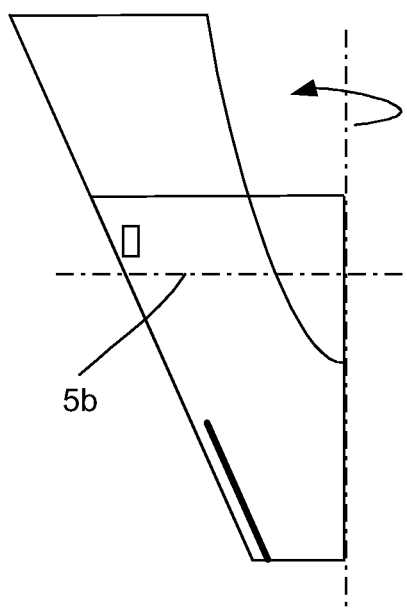
Figure 4C:
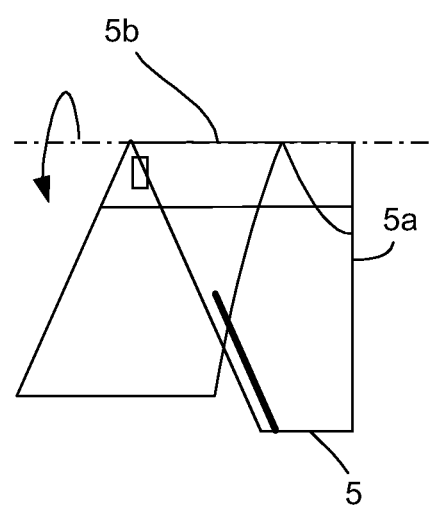

The stool collector 3 can advantageously be folded together one (FIG. 4a), two (FIG. 4b) or preferably three times (FIG. 4c) along the folding lines 5, 5a and 5b, respectively. Hereby, the dimensions of the stool collector 3 are more suited for packing of the stool collector 3, e.g. in a plastic bag.

The rear piece 3a comprises a plurality of perforations 7 intended for allowing air trapped inside the stool collector 3 to escape when the stool collector 3 is flushed in the toilet 2. In FIG. 1a a few perforations 7 have been shown for illustrative purposes. The perforations 7 are in the form of linear cuts in the paper material, having a diameter of about 0.4 mm in diameter and a linear length of about 5-10 mm. There are about five perforations per $cm^2$. Similar perforations may also be provided in other parts of the stool collector 3 such as in the front piece 3b. Perforations may also be provided in the stool collecting area 1, in which case they should be of a diameter sufficiently small to retain faeces from escaping through the perforations, typically a diameter less than 1 mm.

The stool collector 3 further comprises an area with an adhesive 8 adapted for connecting the stool collector 3 to the toilet bowl 2a and/or the toilet seat 2b. The adhesive is arranged at the corners of the rearwards edge of the rear piece 3a. The adhesive is applied to the bottom side so that when the user secures the stool collector 3 to the toilet bowl 2a, it will be prevented from slipping prematurely into the toilet bowl 2a. When the user is seated on the toilet seat 2b, the weight of the user will keep the collector in place allowing a subsequent collection of a stool specimen while still preventing the stool collector 3 from slipping unintentionally into the toilet bowl 2a.

The stool collector 3 is intended for a single use after which it can be flushed in the toilet 2. To ensure that the drain or sewers are not clogged by the rather large stool collector 3, the front piece 3a, rear piece 3b and intermediate piece 3e are manufactured from highly water soluble paper material. The material is also flexible, foldable and biodegradable. "Biodegradable" materials in the context of the present invention are materials amenable to biological degradation when exposed to appropriate conditions. Such biodegradation should generally produce decomposition products that do not pose an environmental threat.

The front piece 3b, rear piece 3a and intermediate piece 3e are cut from one large plane piece of paper. Although this is preferred, it would be possible to compose a stool collector according to the invention from separate pieces of material for example by gluing them together. Several types of paper material may be appropriate, including toilet paper or a type of paper similar to that used for disposable (i.e. flushable) toilet seat covers.

The paper type applied in the present embodiment is in accordance with the ISO 536 standard, implying that when flushed through the toilet into a sewage system the paper attains defibration within 20 minutes, preferably within 8 to 12 minutes, when in contact with the moving water of the sewage system during normal circulation through a common sewage system. The piece of paper from which the stool collector has been cut has a weight of between 23 $g/m^2$ and 50 $g/m^2$.

Experiments have furthermore that a satisfactorily functioning paper material has the following specifications:
- Longitudinal pull strength: At least 1.5, preferably between 1.5 and 4.6, according to the SCAN P-67 standard.
- Transversal pull strength: At least 0.7, preferably between 0.7 and 2.0, according to the SCAN P-67 standard.
- Longitudinal tear strength: At least 125, preferably between 125 and 350, according to the ISO 1974 standard.
- Transversal tear strength: At least 210, preferably between 210 and 450, according to the ISO 1974 standard.

Paper material types like those described in the above are so-called semi wet-strong papers. A stool collector according to the above-described embodiment of the invention manufactured from such papers has been shown experimentally to be able to contain a stool deposition for at least three minutes before the material gives way.

Other suitable materials comprise cardboard and/or paper though materials such as polymers or cloth may also be used if being highly water soluble. Such materials are also preferably biodegradable. The stool collector according to the invention may be manufactured from a combination of different materials taking into account that different material properties may be desired for different parts of the stool collector.

The material(s) making up the stool collector may be coated or impregnated to provide the surface with e.g. an anti-friction coating. Such coatings may comprise various waxes, which are known within the art, and are preferably biodegradable. Thus, the waxes will typically be of a natural origin, such as from a vegetable or an animal source, although biodegradable synthetic waxes may also be appropriate.

The stool collector 3 may be provided in a kit of parts (not shown), which in addition to the stool collector 3 also includes a stool container and/or a spatula as well as a manual with instructions on how to employ the stool collector, including instructions on its mounting and disposal, and a lid or closure mechanism for the stool container. The contents of the kit will normally be packaged together in a box or plastic bag.

When obtaining a stool specimen with the stool collector 3 in an embodiment of the method according to the second aspect of the invention, first the stool collector 3 is taken out of the box or plastic bag, and it is unfolded. Then it is positioned on the upper rim of the toilet bowl 2a of the toilet 2. The stool collector 3 is provisionally attached by means of the adhesive strips 8 adhesively attaching the stool connector 3 at the rear corners of the upper rim of the toilet bowl 2a after which the tip-up toilet seat 2b is lowered to firmly fix the wings 3c, 3d and the rear part 3a between the toilet seat 2b and the toilet bowl 2a. Now, the stool collector 3 is positioned as shown in FIG. 1a with the pocket-like stool collecting area extending into the toilet bowl 2a.

A user (male or female) then sits down on the toilet seat 2b, delivering a stool sample into the pocket-shaped stool collecting area 1. Any simultaneous urination is deposited directly into the toilet bowl 2a through the cut-out 4.

Subsequently, a stool specimen is collected from the stool collecting area 1 by means of a spatula or the like, and the specimen is transferred into a stool container such as a stool tube. When the desired amount of stool has been moved to the stool tube, the latter is removed for analysis in a laboratory or the like.

Finally, the toilet seat 2b is tipped up, and the stool collector 3 and remaining parts of the stool sample (still in the stool collecting area 1) are released into the toile bowl to be flushed into the drain. The stool collector 3 is dissolved in less than 20 minutes, preferably between 8 and 12 minutes, after having been flushed out.

Alternatively, the stool collector 3 is positioned on top of the tip-up toilet seat, the adhesive strips 8 adhesively attaching the stool connector 3 at the rear corners of the toilet seat 2b. However, this embodiment of the method according to the second aspect of the invention may have the disadvantage that the stool collector 3 slides into the toilet bowl 2a when the user stands up after having deposited the stool specimen. To alleviate this problem more and stronger adhesive areas could be provided on the bottom side of the stool collector 3, e.g. both on the front piece 2b and the rear piece 2a.

Also, the stool collector according to the invention may be applied to the toilet types known from southern Europe in which the toilet bowl is integrated into the floor, and the user stands on foot plates when defaecating. In this case the stool collector is similarly mounted on an upper rim of the toilet bowl, this upper rim typically being in the plane of the floor.

The stool collector according to the first aspect of the invention may be used at home by a patient suffering from a condition with which an analysis of a stool specimen may be appropriate for determining the exact condition and finding a suitable means of treatment. Medical, paramedical or other staff at a hospital may also use the stool collector according to the invention for collecting specimens from patients. The nature of the stool specimen from a specific patient will be dependant on the medical condition of the patient. The specimen collector according to the invention is not particularly limited regarding the composition of the specimen, and the collector may be employed for collection of specimens containing up to about 90% liquid, such as may be the case for patients suffering from diarrhea.

When used in a hospital or similar health care facility the stool collector of the invention may simplify the procedure for collecting specimens compared to current procedures, primarily due to its easy disposal. Following deposition of a stool specimen in the stool collector, transferring a specimen to a stool container and flushing the specimen collector in the water closet, the stool container furthermore provides a simple and hygienic means to transport the stool specimen to a laboratory or the like for e.g. analysis of the specimen. Transportation of the specimen contained in the stool container may also be performed by a patient or user having used the stool collector away from a laboratory, e.g. at home, as well as by the hospital staff.

Figure 5:
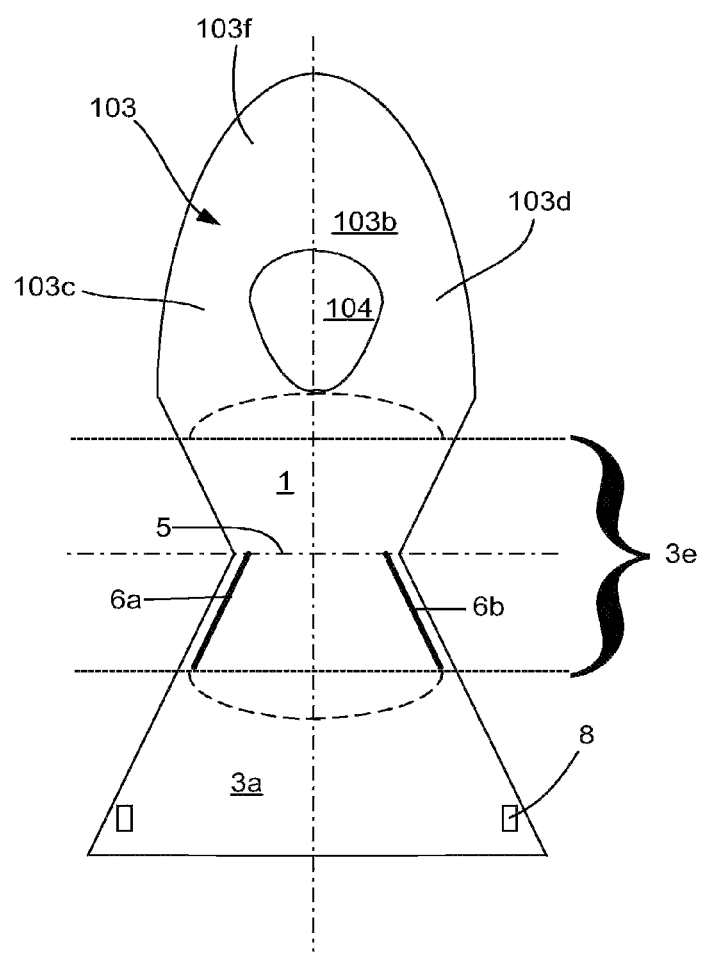
FIG. 5 shows a plane view corresponding to that of FIG. 3 of another embodiment of the stool collector according to the first aspect of the present invention.

FIG. 5 shows another embodiment of a stool collector 103 according to the invention, the reference numbers corresponding to those of the previously described embodiment, but having been added 100. The stool collector is identical to and is used in a similar way as the stool collector 3 above, except as described below.

A front piece 103b of the stool collector 103 comprises two lateral wings 103c, 103d. In contrast to the wings 3c, 3d of the stool collector 3 above, the wings 103c, 103d are connected at a distal end by means of a bridge 103f, the front piece 103 completely enclosing a cut-out 104 providing the urine opening. Hereby, greater strength of the stool collector 103 can be achieved; however, the urine cut-out 104 is not as efficient, and the stool collector 103 is more difficult to position properly on the toilet bowl.

The invention claimed is:

1. A stool collector adapted for being positioned in a use position in which it is secured to a standard water closet or toilet to collect a stool sample delivered by a user,
said stool collector further comprising
a rear piece placed on a rear part of a toilet bowl and adapted for being secured between a rear half of a toilet bowl and a tip-up toilet seat of said toilet,
a front piece adapted for being secured between laterally spaced portions of a front half of said toilet bowl and a front half of said tip-up toilet seat, respectively, said front piece comprising two forward extending laterally spaced wings,
enclosing a cut-out adapted to allow for urine from said user to pass through into said toilet bowl in said use position, and
an intermediate piece connecting said front and rear pieces and in said use position forming a stool collecting area adapted to receive said stool sample,
said front, rear and intermediate pieces are manufactured from a water soluble paper material such as to make said stool collector suitable for being flushed in a standard water closet, wherein the rear piece is wider than each of the forward extending wings, and
at least one of said rear piece and front piece comprise a plurality of perforations suitable for allowing air trapped inside the stool collector to escape when flushed in a water closet.

2. A stool collector according to claim 1, wherein said front, rear and intermediate pieces are manufactured from the same material, and they have been cut from one plane piece of said paper material.

3. A stool collector according to claim 2, wherein said front, rear and intermediate pieces are manufactured from the same material, and wherein they have been cut from one plane piece of said paper material.

4. A stool collector according to claim 2, wherein said intermediate piece is formed by a transverse centre folding, an attachment, formed as a linear gluing line, wherein opposite peripheral portions of said intermediate piece are connected to the attachment to form said stool collecting area, said stool collecting area forms a downwards depression in said use position.

5. A stool collector according to claim 4, wherein said intermediate piece has a transverse dimension equal to or smaller than an associated transverse dimension of said toilet bowl in said use position, such that said intermediate portion in said use position is adapted to hang from said front and rear pieces.

6. A stool collector according to claim 5, further having an axial centre line, preferably a line of symmetry, that extends from a rear edge to a front edge of said stool collector, and wherein, when measured on said stool collector in a non-folded position, i.e. in which said peripheral attachments are released:
said intermediate piece has a length, i.e. a dimension parallel to said centre line between front and rear edges of said peripheral attachment, of 140-360 mm and a largest width measured perpendicularly to said centre line of 320 mm,
said rear piece has a length, i.e. a dimension parallel to said centre line between said rear edge of said peripheral attachment and a rear edge of said stool collector, of 190-270 mm,
said wings have a length, i.e. a dimension parallel to said centre line between said front edge of said peripheral attachment and a front edge of said stool collector, of 200-320 mm, and
said cut-out has a length, i.e. a dimension parallel to said centre line, of 190-270 mm.

7. A stool collector according to claim 4, further having an axial centre line, preferably a line of symmetry, that extends from a rear edge to a front edge of said stool collector, and wherein, when measured on said stool collector in a non-folded position, i.e. in which said peripheral attachments are released:
said intermediate piece has a length, i.e. a dimension parallel to said centre line between front and rear edges of said peripheral attachment, of 140-360 mm, and a largest width measured perpendicularly to said centre line of 320 mm,
said rear piece has a length, i.e. a dimension parallel to said centre line between said rear edge of said peripheral attachment and a rear edge of said stool collector, of 190-270 mm,
said wings have a length, i.e. a dimension parallel to said centre line between said front edge of said peripheral attachment and a front edge of said stool collector, of 200-320 mm, and said cut-out has a length, i.e. a dimension parallel to said centre line, of 190-270 mm.

8. A stool collector according to claim 1, wherein said front and rear pieces comprise edges suitable for being folded down at an exterior of said toilet bowl.

9. A stool collector according to claim 1, wherein said front and rear pieces are adapted for contact with at least 60% of a total circumference of an upper rim of said toilet bowl.

10. A stool collector according to claim 1, wherein said paper material is adapted to defibrate in less than 20 minutes when being flushed in said toilet.

11. A stool collector according to claim 1, wherein said paper material has at least one of the following properties:
   a weight of at least 23 g/m$^2$,
   a longitudinal pull strength of at least 1.5 according to the SCAN P-67 standard,
   a longitudinal tear strength of at least 125 according to the ISO 1974 standard,
   a transversal pull strength of at least 0.7 according to the SCAN P-67 standard, and
   a transversal tear strength of at least 210 according to the ISO 1974 standard.

12. A stool collector according to claim 1, wherein said stool collecting area is provided with an anti-friction coating comprising a biodegradable material.

13. A stool collector according to claim 5, wherein said rear piece comprises a straight rearwards edge, an adhesive adapted for attaching said stool collector to said toilet bowl being provided on said rearwards edge of said rear piece.

14. A stool collector according to claim 13, wherein said adhesive is arranged at the corners of said rearwards edge.

15. A method for obtaining a stool specimen comprising the steps of
   providing a stool collector according to claim 1;
   attaching said stool collector between a toilet bowl and a tip-up toilet seat by securing the rear piece between rear halves of a toilet bowl and the tip-up toilet seat and securing the front piece between front halves of said toilet bowl and said tip-up toilet seat;
   positioning said stool collector in said water closet and keeping the collector in place by pressing the toilet seat onto the collector resting on the rim of the toilet bowl;
   depositing a stool sample in said stool collector;
   transferring a stool specimen to a stool container;
   tipping up the toilet seat, releasing the stool collector and remaining parts of the stool sample, and flushing the stool collector into the drain.

16. A method according to claim 15, wherein said stool collector is dissolved in less than 20 minutes after having been flushed out.

17. A stool collector according to claim 1, wherein each perforation has a diameter of 0.1-1 mm and/or a linear length of 2-50 mm.

* * * * *

UNITED STATES PATENT AND TRADEMARK OFFICE
CERTIFICATE OF CORRECTION

| | | |
|---|---|---|
| PATENT NO. | : 8,615,824 B2 | Page 1 of 1 |
| APPLICATION NO. | : 12/736632 | |
| DATED | : December 31, 2013 | |
| INVENTOR(S) | : Morten Hostrup Sonderholm et al. | |

It is certified that error appears in the above-identified patent and that said Letters Patent is hereby corrected as shown below:

Title page:

Item (73) Assignee, should read:

-GP Medical Devices, ApS, Holstebro, Denmark

Signed and Sealed this
Eighteenth Day of February, 2014

Michelle K. Lee
*Deputy Director of the United States Patent and Trademark Office*